(12) United States Patent
Miyawaki et al.

(10) Patent No.: US 8,133,170 B2
(45) Date of Patent: Mar. 13, 2012

(54) ENDOSCOPE

(75) Inventors: Tetsumaru Miyawaki, Shimane (JP);
Nobuharu Takahashi, Saitama (JP);
Shozo Iyama, Saitama (JP)

(73) Assignees: Tetsumaru Miyawaki, Shimane (JP);
Fujifilm Corporation, Tokyo (JP)

( * ) Notice: Subject to any disclaimer, the term of this patent is extended or adjusted under 35 U.S.C. 154(b) by 372 days.

(21) Appl. No.: 12/406,597

(22) Filed: Mar. 18, 2009

(65) Prior Publication Data
US 2009/0240110 A1 Sep. 24, 2009

(30) Foreign Application Priority Data

Mar. 19, 2008 (JP) .................................. 2008-070644

(51) Int. Cl.
*A61B 1/00* (2006.01)

(52) U.S. Cl. ........ 600/150; 600/139; 600/141; 600/142; 600/144; 600/146; 600/149

(58) Field of Classification Search .................. 600/139, 600/141, 142, 144, 146–150, 152; 604/528, 604/529
See application file for complete search history.

(56) References Cited

U.S. PATENT DOCUMENTS

| | | | | |
|---|---|---|---|---|
| 3,557,780 A | * | 1/1971 | Sato | 600/141 |
| 4,787,369 A | * | 11/1988 | Allred et al. | 600/149 |
| 5,179,935 A | * | 1/1993 | Miyagi | 600/142 |
| 5,462,527 A | * | 10/1995 | Stevens-Wright et al. | 604/528 |
| 5,944,690 A | * | 8/1999 | Falwell et al. | 604/170.03 |
| 6,319,195 B1 | * | 11/2001 | Nakaichi et al. | 600/120 |
| 2002/0099266 A1 | * | 7/2002 | Ogura et al. | 600/139 |
| 2002/0177750 A1 | * | 11/2002 | Pilvisto | 600/146 |
| 2006/0025652 A1 | | 2/2006 | Vargas | |
| 2006/0111616 A1 | * | 5/2006 | Danitz | 600/142 |
| 2007/0015965 A1 | | 1/2007 | Cox et al. | |
| 2007/0021737 A1 | * | 1/2007 | Lee | 606/1 |
| 2007/0270648 A1 | * | 11/2007 | Smith et al. | 600/139 |
| 2008/0027285 A1 | * | 1/2008 | Yasunaga | 600/150 |
| 2008/0039691 A1 | * | 2/2008 | Smith et al. | 600/146 |

FOREIGN PATENT DOCUMENTS

| | | |
|---|---|---|
| EP | 1 849 396 | 10/2007 |
| JP | 2000-126120 | 5/2000 |
| JP | 2002-355217 A | 12/2002 |
| JP | 2005-065931 | 3/2005 |

* cited by examiner

*Primary Examiner* — Thomas J Sweet
*Assistant Examiner* — Kathryn D Sheikh
(74) *Attorney, Agent, or Firm* — Birch, Stewart, Kolasch & Birch, LLP

(57) ABSTRACT

An insertion instrument which is connected to a manipulating head grip is composed of an elongated flexible tube section, an articular section and a rigid tip end section in series from a proximal end which is connected to the manipulating head grip. The articular section can be flexed in an arbitrary direction by way of a flexion control means which is provided on the manipulating head grip. A flexible tube straightening means is provided internally of the flexible tube section to straighten the same into a rectilinear form. The flexible tube straightening means is activated into a straightening action in interlinked relation with a flexing operation of the flexion control means.

11 Claims, 16 Drawing Sheets

ENDOSCOPE

TECHNICAL FIELD

This invention relates to an endoscope for use in medical examinations and treatments, and more particularly to an endoscope which is especially suitable for use as a colonoscope in lower endoscopy.

TECHNICAL BACKGROUND

An elongated flexible insertion instrument of the so-called colonoscope is introduced into the large intestine via the anus and rectum. In order to broaden the examination range, it is desirable for a colonoscope to be able to advance a fore distal end of the insertion instrument as far as the cecum from a depth of the colon. The large intestine includes the sigmoid colon, descending colon, transverse colon and ascending colon, of which the sigmoid colon is in the shape of a three-dimensional loop, taking a very tortuous form in a transitional part to the descending colon. For these reasons, difficulties are usually experienced in introducing a colonoscope into a depth of the colon, passing an insertion instrument of the colonoscope around turns in a three-dimensionally complicated intestinal tract. For passage through such a tortuous path of insertion, the elongated insertion instrument of the colonoscope needs to have a structure which is pliable in a certain degree but stiff enough for transmitting a thrusting force securely from a proximal to fore distal end of the insertion instrument.

In this connection, disclosed in Patent Literature 1 below is an endoscopic insertion instrument which is variable in stiffness in bending directions depending upon the mode of manipulative operation. In an order from a proximal end which is connected to a manipulating head grip, generally an endoscopic insertion instrument is composed of an elongated flexible tube section, an articular flexing section and a rigid distal end section. The flexible tube section is formed of a flexible tubular structure which is flexible in bending directions. In Patent Literature 1, a closely wound stiffness-control coils are extended internally of a flexible tubular structure of a flexible tube section from a proximal end to a fore distal end thereof. Operating wires are passed through the closely wound stiffness-control coils, and a fore end of each operating wire is fixed to a connection ring which is interposed between the flexible tube section and articular flexing section, and a fore end of the stiffness-control coil is fixed to the operating wire. A proximal end of the operating wires is led out of the stiffness-control coil and connected to a push-pull manipulation rod. When the manipulating rod is pulled, adjacent helices of the stiffness-control coil are closed more tightly to each other to stiffen part of the flexible tube section of the insertion instrument. Besides, under the influence of tensioning of the operating wires, the flexible tube section as a whole is compressed and stiffened furthermore.

[Patent Literature 1] Japanese Laid-Open Patent Application 2002-355217

DISCLOSURE OF THE INVENTION

Problem(s) Solved by the Invention

In the case of an endoscopic insertion instrument which is arranged as in Patent Literature 1 above, the stiffness of the elongated flexible tube section of the insertion instrument can be varied suitably after introduction into a body cavity. However, as a matter of fact, it is difficult to pass an endoscopic insertion instrument smoothly through a very tortuous path of insertion in the large intestine simply by controlling stiffness of a flexible tube section alone. As an endoscopic insertion instrument is slid in along an intracavitary wall like the lining wall of the large intestine, the lining wall in contact with the insertion instrument is easily stretched or contracted by the movements of the latter. Accordingly, when a thrust is applied by way of a manipulation means to push forward a flexible tube section when the insertion instrument in a stiffened state, the thrust is transmitted as far as a fore distal end of the insertion instrument to propel the fore distal end of the instrument. However, simultaneously with this propelling movement, the intestinal lining wall comes into intimate contact with outer surfaces of the insertion instrument. As the fore distal end of the insertion instrument is propelled further, the intestinal lining wall is pushed forward in the direction of insertion of the endoscope. Therefore, even if the insertion instrument is in a stiffened state, the passage of insertion is jammed and blocked by the intestinal lining wall, making it difficult to move the insertion instrument further in a forward direction.

By the way, an endoscopic insertion instrument is provided with an articular flexing section between an elongated flexible tube section and a rigid tip end section to aim an endoscopic observation means on the rigid tip end section in a desired direction by remote control from a manipulating head of the endoscope. Accordingly, the rigid tip end section of the insertion instrument can be turned forward in the direction of insertion even in a three-dimensionally twisted passage in the sigmoid colon or in an acutely curved transitional passage from the descending colon to the transverse colon or from the transverse colon to the ascending colon. A problem that one faces in passing an endoscopic insertion instrument into the colon is that the insertion instrument is put in intimate contact with the intestinal lining wall. That is to say, in order to improve maneuverability of an endoscopic insertion instrument in the colon, it is important to control the posture of the instrument in such a way as to keep its outer surfaces out of intimate contact with the lining wall which tends to entangle around the instrument.

The above-mentioned articular flexing section can be utilized for keeping an endoscopic insertion instrument out of intimate contact with intestinal lining walls. Namely, an endoscopic insertion instrument can be passed smoothly forward in the colon by flexing the articular portion in an upward or downward direction or in a rightward or leftward direction in such a way as to keep exterior surfaces of the instrument out of intimate contact with the lining wall. In short, from the standpoint of lessening pains on the part of a patient, it is undesirable to forcibly puss-push in the endoscopic insertion instrument forward in passing a tortuous intestinal tract like the colon.

In the event a fore rigid tip end of an endoscopic insertion instrument gets stuck in an intestinal tract, failing to make a movement in a forward direction despite pushing efforts, a reserve of stretchability potential in the form of a curved bend is formed in a fore end portion of the flexible tube section. Under such circumstances, if the bend in the insertion instrument is straightened into a rectilinear or into an almost rectilinear form for the purpose of bringing the insertion instrument out of intimate contact with the entangling intestinal lining wall while restricting movements of the instrument portions on the proximal side of the bend, the fore rigid tip end section of the instrument can be smoothly moved in a forward direction along the path of insertion.

In the endoscopic manipulation techniques just mentioned, it is important not to stiffen or harden the flexible tube section of the insertion instrument. Those portions of the insertion instrument, on the proximal side of a bend, should rather be held in a restricted state while straightening a fore end portion of the flexible tube section concurrently with flexion of the articular section. In this regard, the insertion instrument can be partially held in a restricted state through utilization of an endoscopic aspiration means, namely, by evacuating the intestinal tract by the use of an endoscopic aspiration means. By so doing, intestinal lining walls forward of the rigid tip end of the insertion instrument become barely restrictive of a forward movement of the insertion instrument upon flexing the articular section. Thus, the rigid distal end of the insertion instrument can be advanced forward along the path of insertion by straightening the flexible tube of the instrument in relation with the flexing operation on the articular section. However, endoscopes which are currently in use in medical fields are not equipped with a function of straightening a bend in a flexible tube section of an insertion instrument into a rectilinear or near rectilinear form.

SUMMARY OF THE INVENTION

In view of the foregoing situations, it is an object of the present invention to provide an endoscope particularly suitable for use in colonoscopy, which is equipped with a flexible tube straightening means internally of an elongated flexible tube section of an insertion instrument to straighten a curved bend in the flexible tube section in relation with an operation of flexing an articular section of the insertion instrument.

It is another object of the present invention to provide an endoscope which is capable of straightening a bend in a flexible tube section of an endoscopic insertion instrument in relation with a flexing operation for an articular section of the instrument, thereby assisting advancement of the insertion instrument through a path of insertion while restricting interlinked straightening actions to permit ordinary flexing operations in an unaffected state.

It is still another object of the present invention to provide an endoscope which is particularly suitable for use as a colonoscope and capable passing an insertion instrument smoothly through three-dimensionally complicate contours in long and tortuous passages of the large intestine.

It is a further object of the present invention to provide an endoscope which is particularly suitable for use as a colonoscope and capable of getting an insertion instrument out of jamming intestinal lining walls by a simple operation.

In order to achieve the above-stated objectives, according to the present invention, there is provided an endoscope having an insertion instrument for introduction into a body cavity, the insertion instrument being connected at a proximal end to a manipulating head grip and being composed of an elongated flexible tube section, an articular section and a rigid tip end section in series from said proximal end, the articular section being angularly flexed in a desired direction by way of a manual flexion control means on the manipulating head grip, characterized by the provision of: a flexible tube straightening means incorporated into the flexible tube section to straighten up a curved bend in the flexible tube section on the proximal side of the articular section; the straightening means being coupled with the flexion control means via an interlinking mechanism adapted to activate and deactivate the straightening means in interlinked relation with a flexing operation by the flexion control means.

The flexible tube straightening means can be constituted by a traction wire. At a fore distal end, the traction wire is fixedly connected to an internal portion of the flexible tube section or to a joint portion with the articular section of the insertion instrument. In case the traction wire is connected to an internal part of the flexible tube section, the position of connection should be as close as possible to a fore distal end of the flexible tube section. The traction wire is internally threaded along a tubular structural member of the flexible tube section at a predetermined radial or angular position. Generally, as a structural member, the flexible tube section employs a double coil tube consisting of two layers of oil tubes which are each formed by helically winding a metal strip in a different direction relative to the other one. In a preferred form of the invention, wire threading pipes are attached on the inner periphery of an inner coil tube to provide an axial guide passage for threading a traction wire at a predetermined radial position in the flexible tube section. The wire threading pipes, also serving as positioning members, may be attached on each helix of the inner coil tube or at intervals of a plural number of helices of the coil tube. A proximal end portion of the traction wire is extended into a casing of the manipulating head grip and wrapped around a straightening pulley. By rotation of the straightening pulley, the traction wire is taken up onto the pulley and brought into a tensioned state.

A flexion control means is provided on the manipulating head grip thereby to flex the articular section of the insertion instrument in a desired direction. The flexion control means can be constituted by a flexing wire having a fore end thereof fixed to a fore distal end of the articular section (or rigid tip end section), a flexing pulley around which a proximal end portion of the flexing wire is wrapped, and a rotational shaft which is rotationally coupled with the flexing pulley. A manual flexion control knob is attached to an outer end of the rotational shaft which is projected on the outer side of the casing of the manipulating head grip. By way of the manual flexion control means, the articular section of the insertion instrument is flexed at least in one direction, preferably in upward and downward directions, and more preferably in upward, downward, rightward and leftward directions.

Similarly to the flexion control means described above, the flexible tube straightening means can employ a traction wire. A single traction suffices to straighten the flexible tube section, and, instead of taking the traction wire onto a straightening pulley, it may be connected to a linearly moving traction member. In case a straightening pulley is employed for taking up the traction wire, it can be coupled with the flexing pulley to put the flexible tube tightening means into and out of a tightening action in interlinked relation with a flexing operation by the flexion control means. It suffices to provide a single flexing pulley in a case where the articular section needs to be flexed in one or two directions. In this case, the flexing pulley and the straightening pulley are provided on one integral assembly. It becomes necessary to provide a couple of flexing pulleys in a case where the articular section needs to be flexed in four directions. In this case, the straightening pulley is coupled with a flexing pulley which is turned at the time of flexing the articular section in a direction away from an intestinal lining wall clinging to exterior surfaces of the insertion instrument. Based on positional relations between an operator and a patient, a flexible tube straightening operation is interlinked with a flexing operation in an upward, downward, rightward or leftward direction. Considering that normally the articular section of the insertion instrument is flexed mostly in upward and downward directions when passing the insertion instrument through an intestinal tract, it is desirable to couple the straightening pulley with a flexing pulley which is allotted to upward and downward flexing operations.

In a case where it is invariably required to straighten up a bend in the flexible tube section simultaneously with a flexing operation, rotation of the straightening pulley can be interlinked with that of a flexing pulley. However, normally the flexion control means alone is manipulated mostly at the time of passing the insertion instrument into a body cavity. Therefore, it is desirable to make arrangements such that the flexion control means can be manipulated independently without exerting influence on the flexible tube section to any material degree. In this regard, preferably the flexible tube straightening means is arranged in such a way as to let the straightening pulley start a straightening action with a delay from a start of a flexing operation by a flexing pulley, instead of starting the straightening pulley simultaneously with the flexing pulley. For this purpose, the traction wire which is wrapped on the straighten pulley is provided with a play in length thereby to delay a straightening action relative to a flexing action. The traction wire of the straightening means is normally left in a slackened state in an undesirable manner due the provision of a play in length. Such a slack in the traction wire can be absorbed by insertion of a slack-absorption member between fore and proximal end portions of the wire.

In another embodiment of the invention, instead of coupling a straightening pulley with a flexing pulley, the straightening pulley is provided separately from the latter and rotationally driven by an electric motor. In this case, the straightening pulley may be put in rotation simultaneously with a flexing pulley. However, it will be desirable for an operator to be able to select either an interlinked mode or a non-interlinked mode, i.e., an interlinked mode in which a straightening pulley is put in a straightening action in interlinked relation with rotation of a flexing pulley or a non-interlinked mode in which the straightening pulley is put out of interlinked relation with the flexing pulley. For instance, a mode selector switch may be provided on a casing of the manipulating head grip for this purpose, thereby to switch the drive motor to and from an interlinked position and a non-interlinked position. Of course, it is possible to make arrangements such that the drive motor is started when the flexing pulley has been rotated through a predetermined angle.

The above and other objects, features and operational effects of the present invention will become apparent from the following particular description of preferred embodiment, taken in conjunction with the accompanying drawings. Needless to say, the present invention is not limited to particular forms exemplified in the drawings.

BEST MODE FOR CARRYING OUT THE INVENTION

Figure 1:
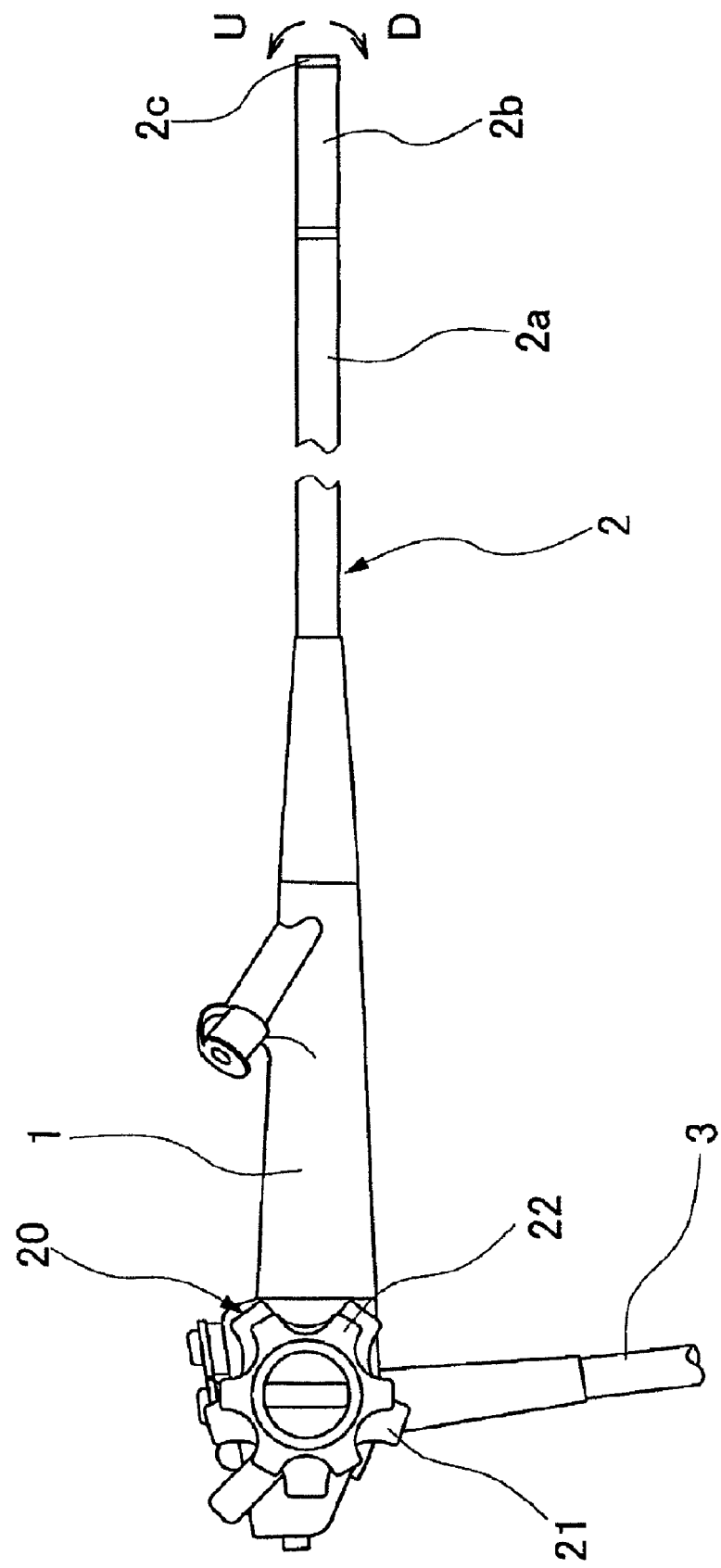
FIG. 1 is a schematic illustration showing the general layout of an endoscope embodying the present invention.

Hereafter, with reference to the accompanying drawings, the present invention is described more particularly by way of its preferred embodiments. Referring first to FIG. 1, there is shown general layout of an endoscope embodying the present invention. In that figure, indicated at 1 is a manipulating head grip of the endoscope, at 2 an insertion instrument, and at 3 a universal connection cable. The insertion instrument 2 includes an elongated flexible tube section 2a which is extended forward from the manipulating head 1 over a predetermined length and flexible in bending directions according to turns in and along a path of insertion. The flexible tube section 2a is contiguously ensued by an articular flexing section 2b, which is in turn ensued by a rigid tip end section 2c. Although omitted in the drawing, an illumination window or illumination windows and an outlet of a tool introduction channel are provided in a casing of the rigid tip end section 2c. The rigid tip end section 2c can be turned to a desired direction by way of the articular section 2b which can be flexed in upward, downward, rightward or leftward direction from a remote control means on the manipulating head 1.

Figure 2:
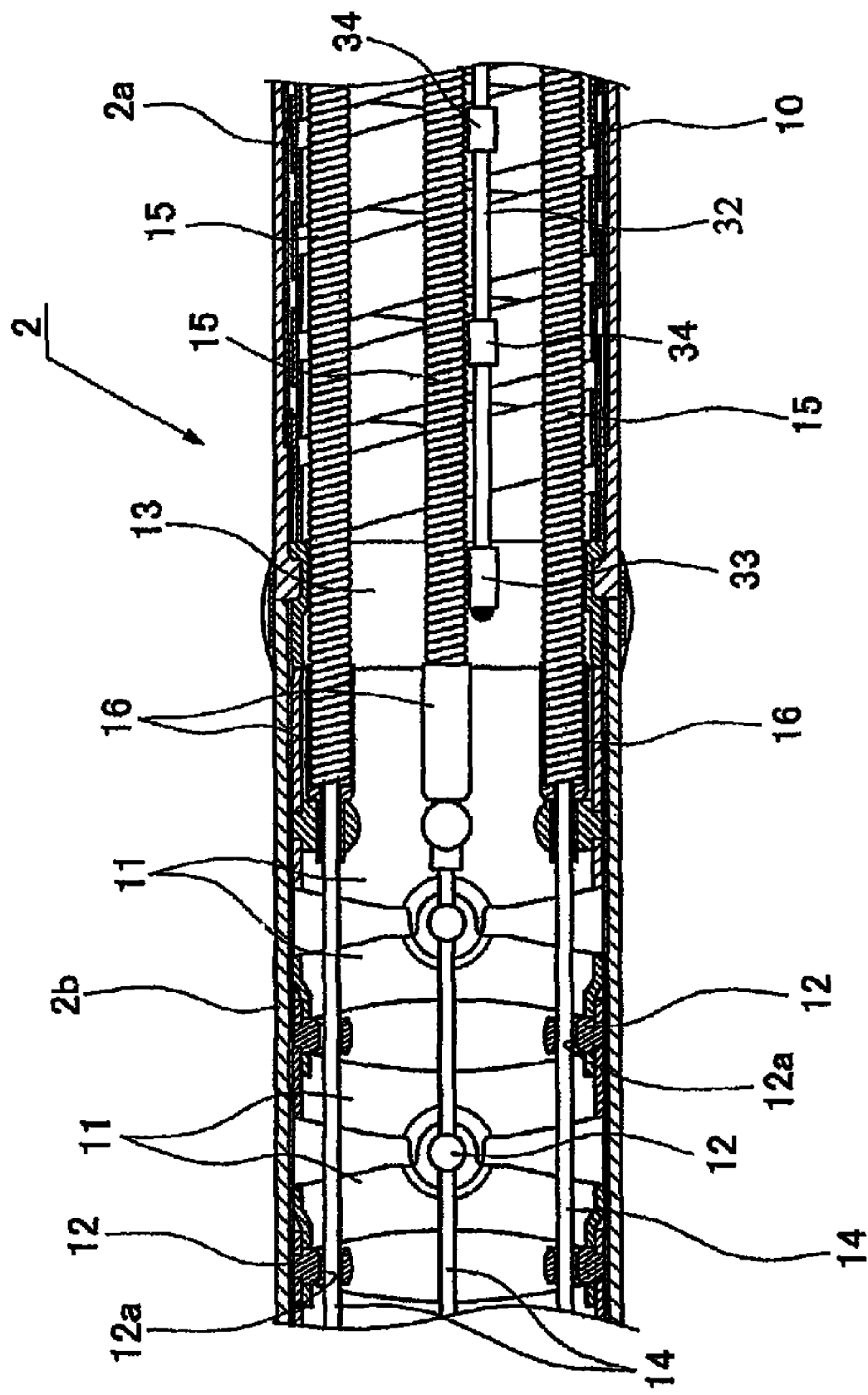
FIG. 2 is a schematic sectional view of a connecting portion between an articular flexing section and a flexible tube section of an endoscopic insertion instrument.
Figure 3:
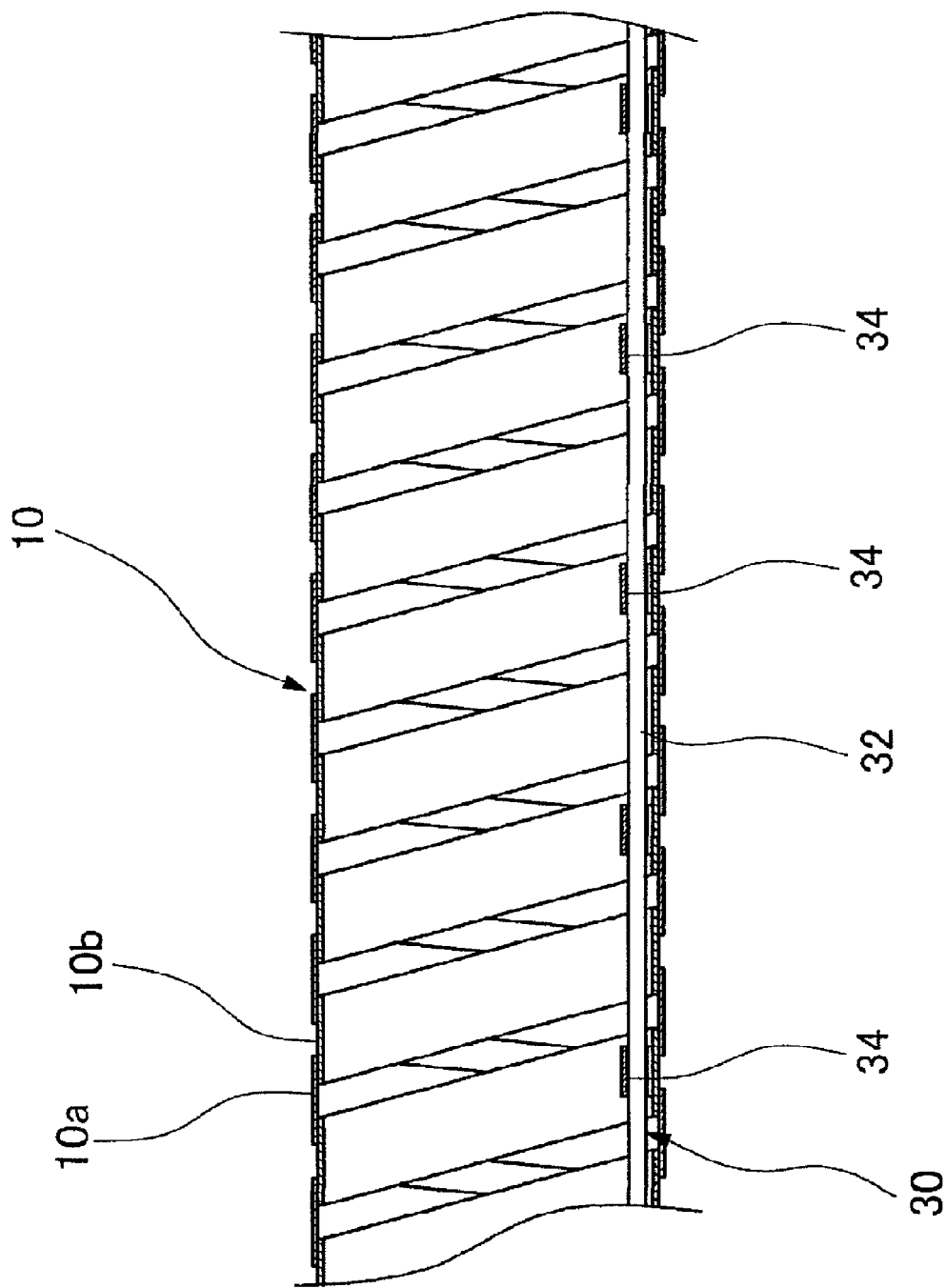
FIG. 3 is a longitudinal sectional view showing the construction of the flexible tube section, along with a guide way for a traction wire.

As seen in FIGS. 2 and 3, the elongated flexible tube section 2a of the insertion instrument 2 has a double coil tube 10 as a structural member, including an outer coil tube 10a and an inner coil tube 10b each in the form of a coil of a metal strip wound in a predetermined pitch. The articular section 2b is composed of a series of articular rings 11 which are articulated successively at right and left and top and bottom articular joints. The fore distal end of the double coil tube 10 is connected to a proximal articular ring 11 by a connector ring 13.

The flexible tube section 2a is bent when a bending load is applied thereto, while the articular section 2b is flexed arbitrarily by a flexing operation. More particularly, the articular section 2b is flexed by remote control from the manipulating head 1. For this purpose, four flexing wires 14 are threaded through the flexible tube section 2*a* at uniformly spaced angular positions, namely, at intervals of 90 degrees in the radial direction. These flexing wires 14 are fixed to an inner periphery of a foremost articular ring in the respective uniformly spaced angular positions. In the articular section 2*b*, each flexing wire 14 is passed through positioning holes 12*a* which are formed axially in respective pivot pins 12. In the flexible tube section 2*a*, the flexing wires 14 are each sheathed in a tightly wound coil tube 15 which is connected to a pipe member 16, which is fixed on the connector ring 13. In the following description, for the convenience of explanation, the four flexing wires 14 which are allotted to the positions for upward, downward, leftward and rightward articular flexions are labeled with reference numerals 14U, 14D, 14L and 14R, respectively.

Figure 4:
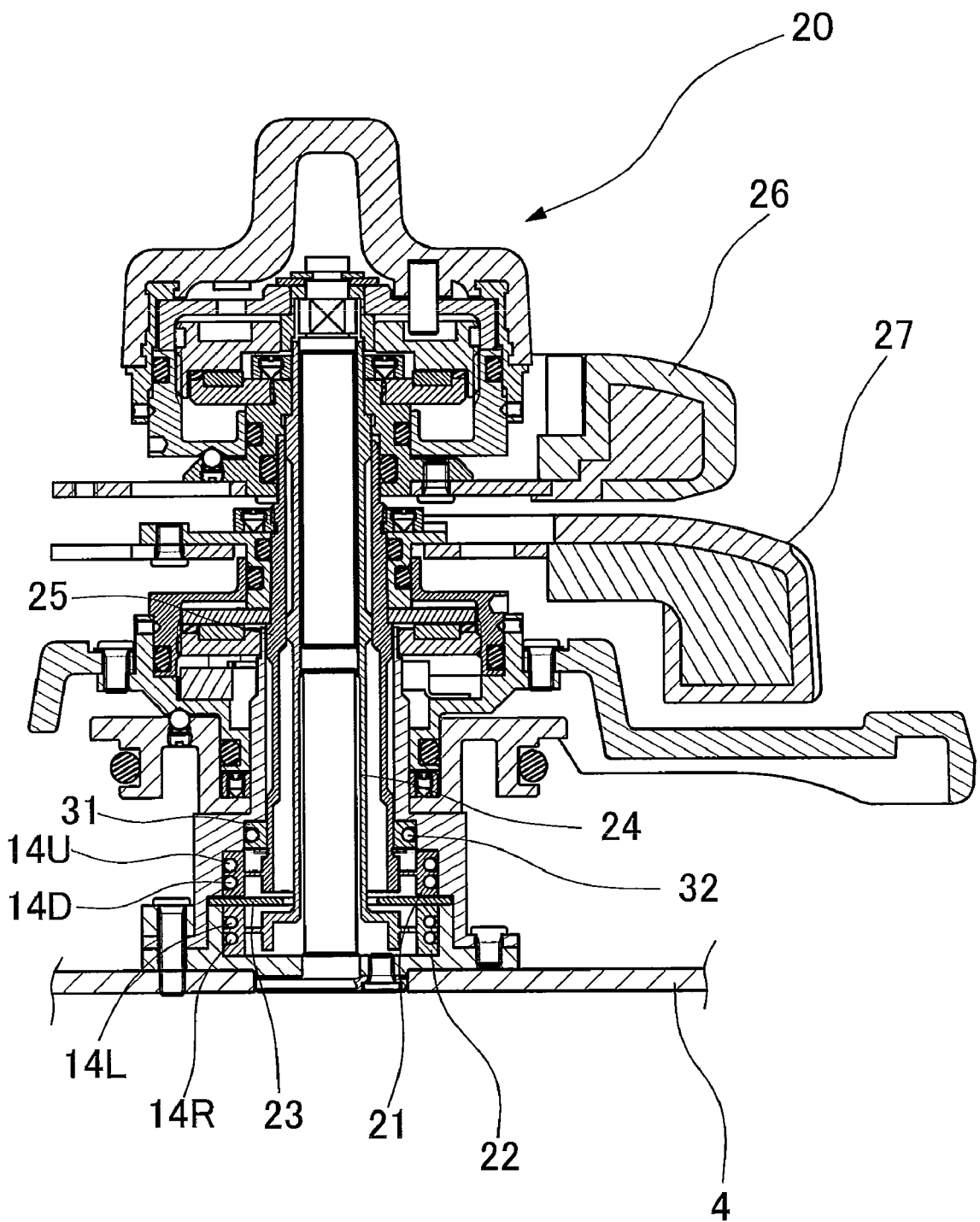
FIG. 4 is a sectional view showing arrangements of a flexion control means.

Shown in FIG. 4 is a manual articular flexion control means which is manipulated to turn the articularly flexing section 2*b* in upward, downward, leftward or rightward direction by pushing or pulling the flexing wires 14. The articular flexion control means 20 is supported on a support plate 4 which is provided internally of the manipulating head 1 of the endoscope, and largely constituted by a first flexing pulley 21 around which a pair of upward and downward flexing wires 14U and 14D are wrapped, and a second flexing pulley 22 around which a pair of rightward and leftward flexing wires 14R and 14L are wrapped.

The first and second flexing pulleys 21 and 22 are mounted in position on the upper and lower sides of a spacer plate 23. The first flexing pulley 21 on the upper side plays a role of turning the articular section 2*b* of the insertion instrument 2 in upward and downward directions, while the second flexing pulley 22 on the lower side plays a role of turning the articular section 2*b* in leftward and rightward directions. For these purposes, the second flexing pulley 22 is connected to an inner rotatable shaft 24 while the first flexing pulley 21 is connected to an outer rotatable shaft 25. These inner and outer shafts 24 and 25 are disposed coaxially with each other, and projected out of a casing of the manipulating head 1. The projected outer end of the outer shaft 25 is connected to a first flexion control knob 26, while the projected outer end of the inner shaft 24 is connected to a second flexion control knob 27. Thus, as the knobs 26 and 27 are manipulated by fingers of operator's hand which grips the manipulating head 1 of the endoscope, the first and second flexing pulleys 21 and 22 are turned, pushing or pulling the flexing wires 14 to flex the articular section 2*b* in a desired direction by remote control from the manipulating head 1.

Figure 5:
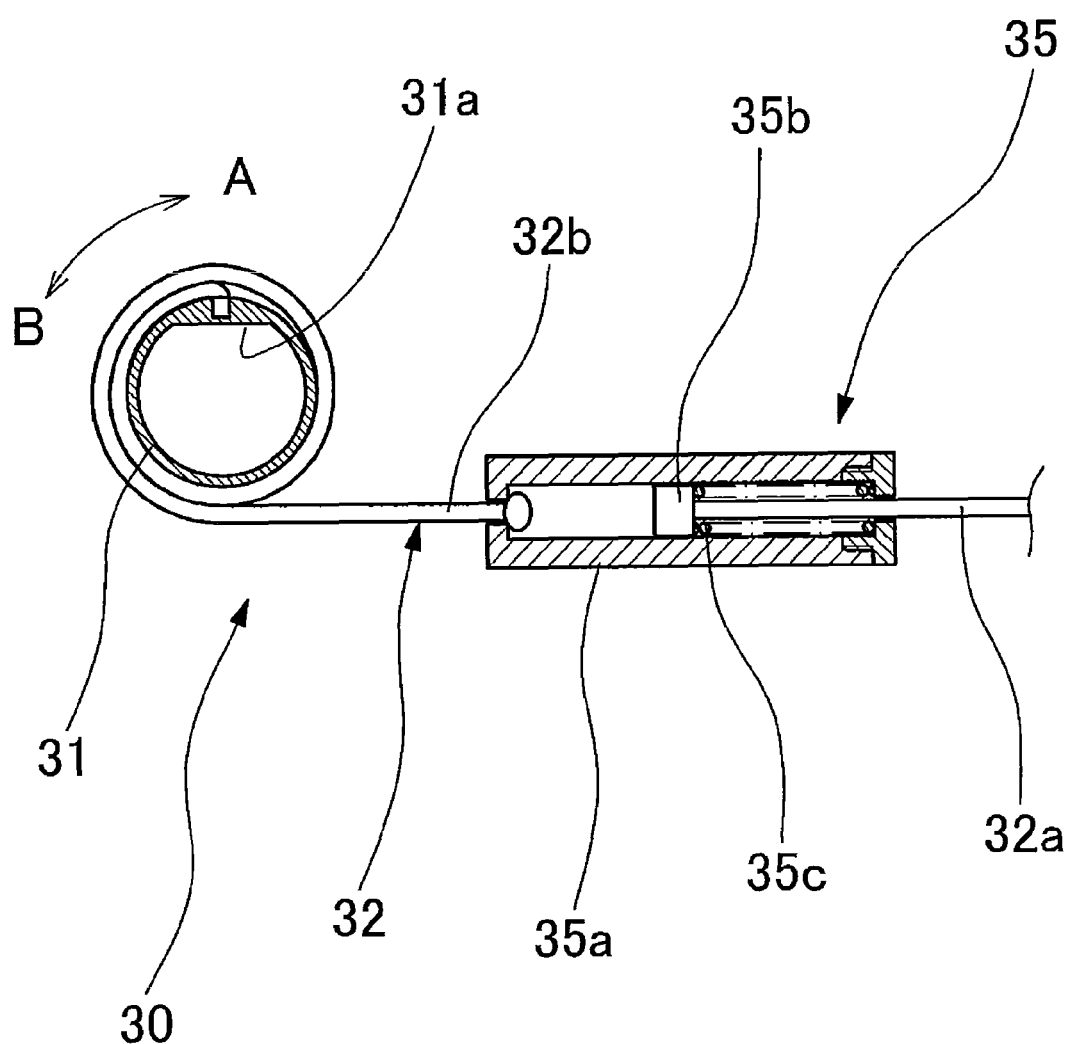
FIG. 5 is a schematic illustration showing particulars of a flexible tube straightening means.

Different from the articular section 2*b*, the flexible tube section 2*a* of 11 the insertion instrument 2 cannot be bent by way of a manipulation means. The flexible tube section 2*a* is bent by external forces. However, according to the present invention, as shown in FIG. 5, the endoscope is provided with a flexible tube straightening means 30 for the purpose of straightening up a bend in the flexible tube portion 2*a*. This flexible tube straightening means 30 is constituted by a traction wire 32 with a proximal end portion wrapped around a straightening pulley 31. This straightening pulley 31 is rotationally coupled with the first flexing pulley 21, in such a way that the traction wire 32 is taken onto the straightening pulley 31 when the first flexion control knob 26 is turned in one direction.

The traction wire 32 is extended forward from the manipulating head 1 as far as a fore distal end of the flexible tube section 2*b* of the insertion instrument 2. At a fore distal end, the traction wire 32 is securely anchored on a fixed pipe 33. The traction wire 32 is threaded through positioner pipes 34 which are provided internally of the inner coil tube 10*b*, a structural member of the flexible tube section 2*b*, at predetermined intervals in the axial direction and at a predetermined angular position in the radial direction of the inner coil tube 10*b*. A base or proximal end portion of the traction wire 32 is wrapped around the straightening pulley 31 within a casing of the manipulating head 1.

As clear from FIG. 5, in a neutral state, the traction wire 32 is wrapped around the straightening pulley 31 by a plural number of turns. As the straightening pulley 31 is rotated in the direction of arrow A, the traction wire 32 is taken up on the straightening pulley to produce a tensile force in the wire. On the other hand, when the straightening pulley 31 is rotated in the direction of arrow B, the traction wire 32 is unwound from the straightening pulley 31 and left in a slackened state. The straightening pulley 31 which is fitted on the outer shaft 25 is blocked against rotation relative to the latter by a flattened portion 31*a* which is formed on part of its inner periphery. Accordingly, by blocking rotation relative to the outer shaft 25, the flattened portion 31*a* functions as a coupling mechanism between the straightening pulley 31 and the first flexing pulley 21.

In this instance, by the first flexion control knob 26, the straightening pulley 31 is turned along with the flexing pulley 21 to take up or unwind the traction wire 32 on or from the straightening pulley 31. In the particular embodiment shown, the traction wire 32 is taken up onto the straightening pulley 31 when the articular section 2*b* is turned or flexed in a downward direction, namely, in the direction of arrow D in FIG. 1. When flexed in the direction of arrow U in the same figure, the traction wire 32 is unwound from the straightening pulley 31 and left in a slackened state. Accordingly, a curved bend in the flexible tube section 2*a* is unbent and straightened into a rectilinear form as soon as the first flexion control knob 26 is manipulated in such a way as to turn the articular section 2*b* in a downward direction.

As long as the first flexion control knob 26 is in a neutral position, the flexible tube section 2*a* remains in a freely bendable state, producing no tension in the traction wire 32 when bent in any direction. This is because the traction wire 32 has an extra length, i.e., a play in length in the wire portion which is unwound from the straightening pulley 31. Therefore, when the flexible tube section 2*a* is bent in a direction of producing tension in the traction wire 32, it remains in a freely bendable state until the play in length of the traction wire is absorbed entirely by a downward flexing action. That is to say, even if the articular section 2*b* is flexed in a downward direction, the flexible tube section 2*a* remains in a bent form until the play in length of the traction wire 32 is absorbed completely. If the articular section 2*b* is flexed beyond a point of complete eradication of the play in length of the traction wire 32, a tension is produced in the traction wire 32 thereby to straighten up a bend in the flexible tube section 2*a*, if any.

The traction wire 32 may be left in a slackened state, but it is preferable to absorb a slack in the traction wire 32 by the use of a slack-absorber 35 as shown in FIG. 5. More particularly, in this case, the traction wire 32 is divided into a fore wire section 32*a* and a proximal wire section 32*b* from the straightening pulley 31, which are interconnected by a slack-absorbing connector tube 35*a*. One wire section, for example, the proximal wire section 32*b* on the side of the straightening pulley 31 is fixedly tied to the connector tube 35*a*, and the other fore wire section 32*a* is connected to a slider member 35*b* which is axially slidably fitted in the connector tube 35. The slider member 35*b* is constantly biased in a direction toward the rear wire section 32*b* by the action of a compression spring 35*c*, that is, in a direction of absorbing a slack in the traction wire 32. Thus, a play in length of the traction wire 32 is absorbed by the slack-absorber 35. Although the slack-absorber 35 may be provided internally of the endoscopic insertion instrument 2, it is desirable to locate same within a casing of the manipulating head 1 where one can find an installation space for the slack-absorber more easily.

In this instance, due to the existence of the slack-absorber 35 which is arranged to take up a play in length of the traction wire, the straightening pulley 31 starts to take up the traction wire 32 with a time delay relative to a start of a rotational movement of the first flexing pulley 21 when the first flexion control knob 26 is turned to flex the articular section 2b. Besides, the straightening pulley 31 is smaller in diameter than the first flexing pulley 21, so that, when the first flexion control knob 26 is turned, the traction wire 32 is taken up by the straightening pulley 31 at a smaller rate as compared with a take-up rate of the flexing wire 14 by the first flexing pulley 21. Therefore, when flexing the articular section 2b, straightening of the flexible tube section 2a does not take place in an interlinked relation with the flexing operation and no load is applied to the flexible tube section 2a when the articular section 2b is flexed through a small angle, which corresponds to the play in length of the traction wire 32. Thus, the slack-absorber 35 virtually has no influences on ordinary flexing operations of the articular section 3b.

Figure 6:
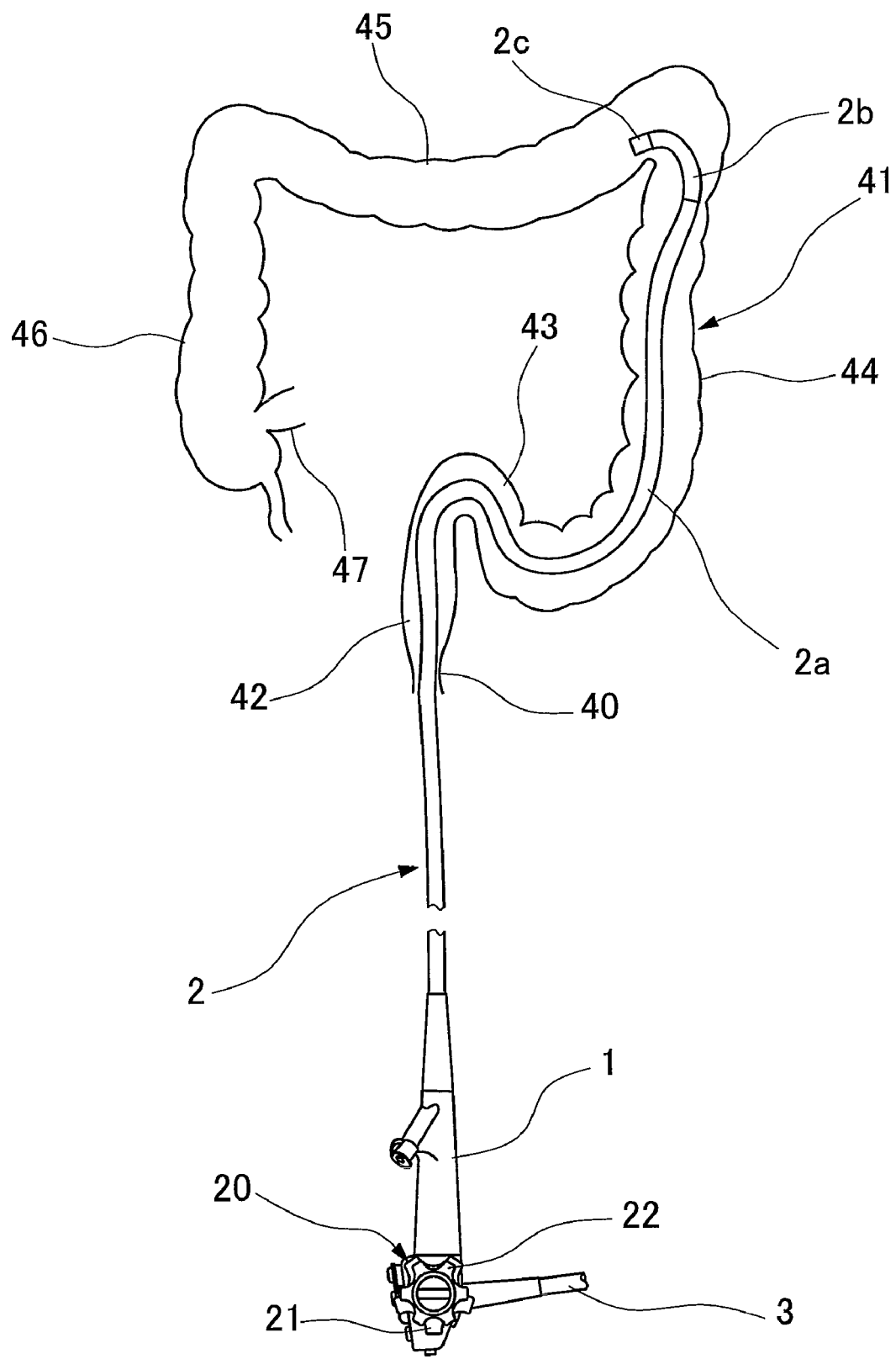
FIG. 6 is a schematic illustration of an endoscope having the insertion instrument introduced into the large intestine.
Figure 8:
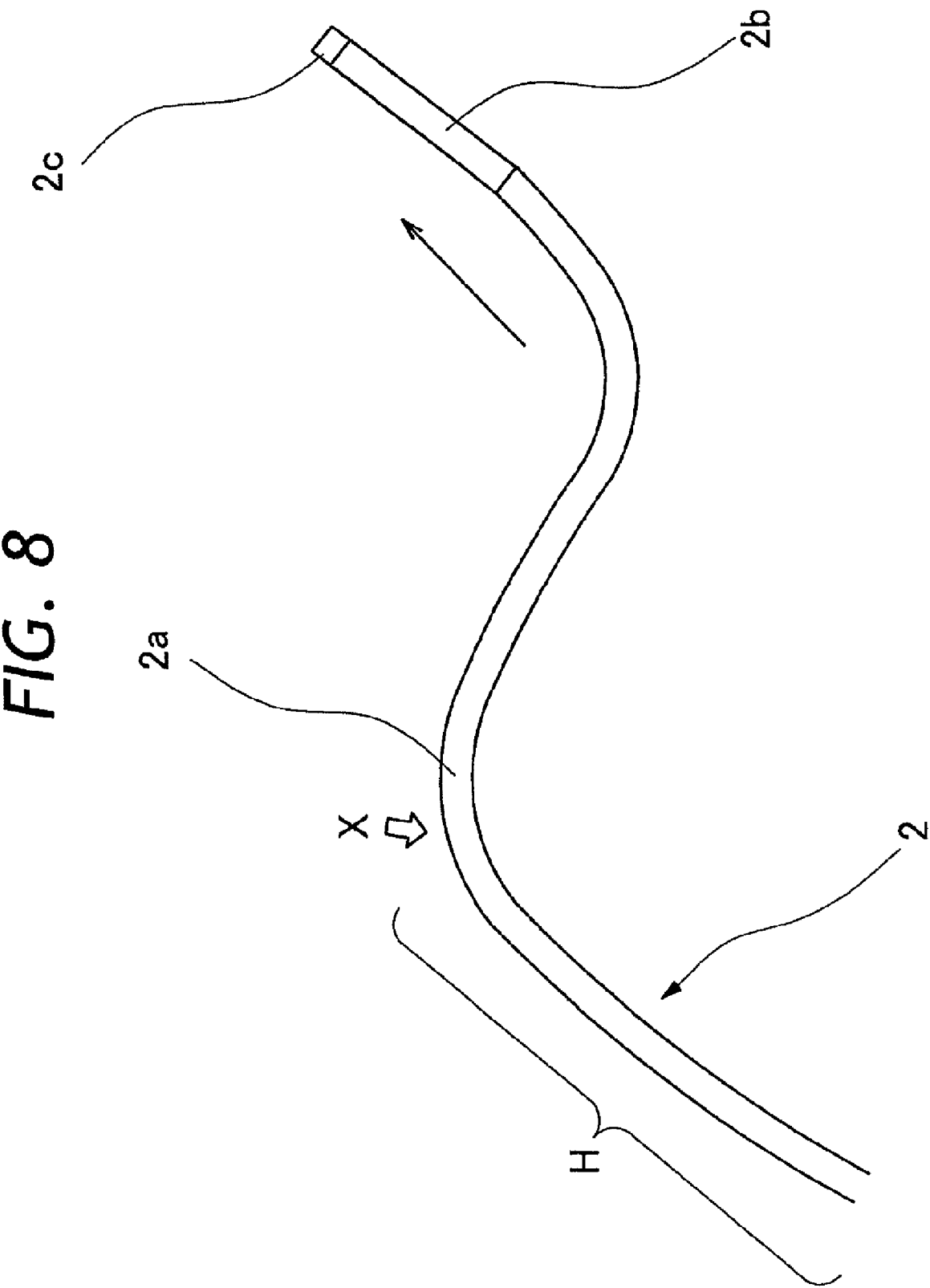
FIG. 8 is a schematic illustration explanatory of a second stage of the manipulation procedure by which the insertion instrument is moved forward by straightening a bend in the flexible tube section.
Figure 9:
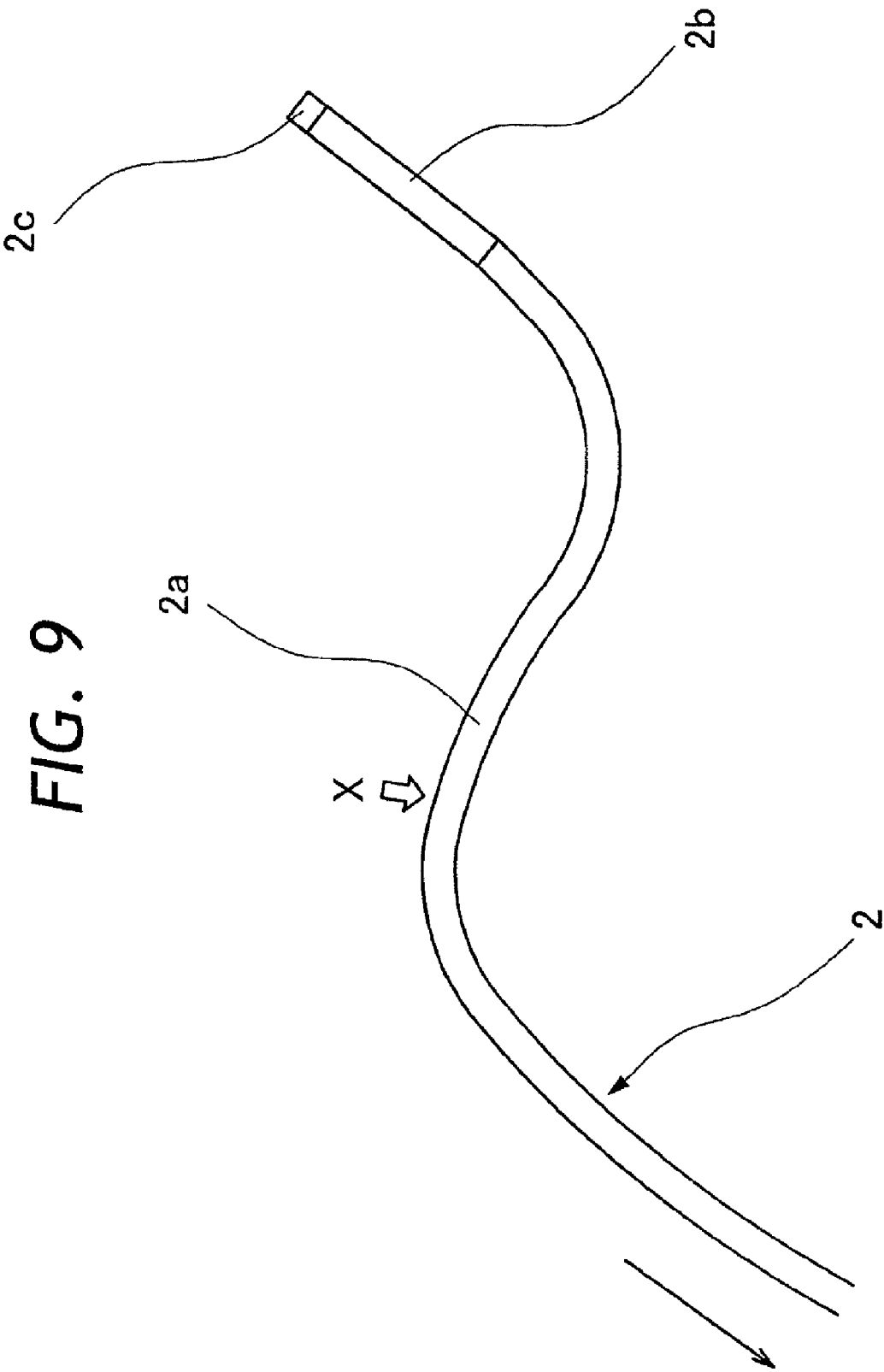
FIG. 9 is a schematic illustration explanatory of a third stage of the manipulation procedure by which the insertion instrument is moved forward while straightening a bend in the flexible tube section.

The endoscope, with the arrangements as described above, is particularly suitable for application, for example, as a colonoscope for examining and treating lining walls in the large intestine. Namely, for examination of the large intestine, for example, the endoscopic insertion instrument 2 is introduced into the large intestine 41 through the anus 40 as shown in FIG. 6. The large intestine 41 includes the rectum 42, sigmoid colon 43, descending colon 44, transverse colon 45, ascending colon 46 and cecum 47. As seen in the drawing, the sigmoid colon 43, drawn in a bent form, is actually in the form of a loop structure which is curved largely in a direction perpendicular to the face of FIG. 6, i.e., a very tortuous and complicate three-dimensional passage. The transitional part from the descending colon 44 to the transverse colon 45 is bent at an angle larger than 90 degrees. Similarly, the transitional part from the transverse colon 45 to the descending colon 46 is bent at an acute angle. Now, in the manner as described below with reference to FIGS. 7 through 9, the endoscope is manipulated to pass the insertion instrument 2 through and along the sigmoid colon 43. The rigid tip end section 2c at the fore distal end of the endoscopic insertion instrument 2 can be propelled smoothly from the anus 40 to the rectum 42 by gripping and pushing in the insertion instrument 2 along a substantially straight path of insertion.

After moving the fore distal end of the insertion instrument 2 from the rectum 42 to the sigmoid colon 43, the insertion instrument 2 is pushed in further by flexing the articular section 2b and gripping an outer portion of the instrument in a loop or loops if necessary. At this time, the lining wall of the sigmoid colon is pushed forward in the direction of insertion in step with advancement of the insertion instrument 2. As a result, the insertion instrument 2 is blocked by a lining wall portion which covers up a distal end face of the rigid tip end section 2c, impeding further advancement of the insertion instrument 2.

Figure 7:
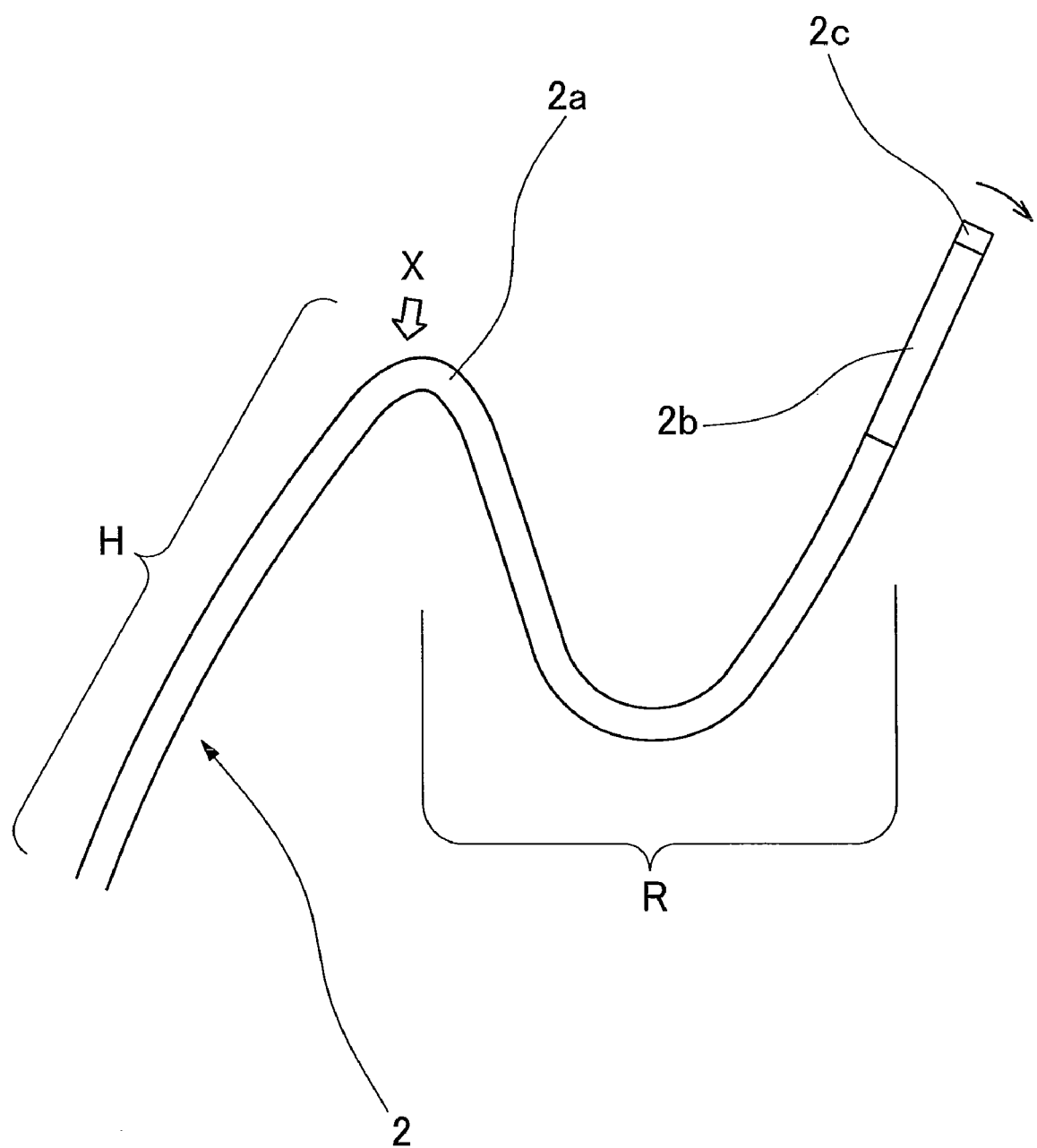
FIG. 7 is a schematic illustration explanatory of a first stage of a manipulation procedure by which the insertion instrument is moved forward by straightening a bend in the flexible tube section.

On such an occasion, the insertion instrument is released from a blocking lining wall of the intestinal tract with an aid of assisting functions. In the first place, the intestinal tract is evacuated by the use of an aspirator which is built in the endoscope. As a result of evacuation of the intestinal tract, lining walls of the tract come into intimate contact with outer surfaces of the insertion instrument. At this time, however, an unblocked passage is opened ahead of the rigid tip end 2c of the insertion instrument 2. In the sigmoid colon 43 of the large intestine 41, actually the intestinal lining walls come into intimate contact with the insertion instrument on the proximal side of a supporting point X which is shown in FIG. 7, namely, between the rectum 42 or a posterior position in the sigmoid colon 43 and the anus 40. In this state, if the insertion instrument 2 is pushed in continuedly, it is met by a resistance and bent into a curved shape within the sigmoid colon 43. Accordingly, the insertion instrument 2 is put in intimate contact with lining walls of the intestinal tract between the anus 40 and a point at a certain depth of the sigmoid colon 43, with a fixed or immobilized portion H of FIG. 7 on the hind side and a stretchability potential reserve R including a curvedly bent portion of the flexible tube section 2a on the fore side.

In this state, utilizing FNP (Fine Network Pattern) of the large intestine as an indicator, the first flexing knob 26 of the flexion control means 20 is manipulated, for example, in such a way as to flex the articular section 2b in an upward (downward) direction or in a rightward (leftward) direction as shown in FIG. 7 to turn the fore distal end of the insertion instrument 2 in a vertical direction of FNP, that is, forward in the direction of advancement of the insertion instrument 2. Whereupon, the fore distal end of the insertion instrument 2 is swung away from the intestinal lining wall, and released from a pushing action of the forwardly displaced intestinal lining wall, and the flexible tube section 2a returns to a natural state by its resiliency. At this time, in interlinked relation with the downward flexion of the articular section 2b by rotation of the first flexing pulley 21, a tension is produced in the traction wire 32 of the flexible tube straightening means 30 by rotation of the straightening pulley 30, driving the flexible tube 2a into a rectilinear form (or into an almost rectilinear form). The elongated insertion instrument 2 stays as a immobilized part H on the proximal side of the stretchability potential reserve R, while a resistance against its advancement of the insertion instrument 2 in the forward direction has been minimized by the flexion of the articular section 2b in a direction away from the intestinal lining wall. Therefore, as shown particularly in FIG. 8, upon straightening the flexible tube section 2a forward of the supporting point X at the boundaries of the stretchability potential reserve R with the immobilized part H, the bent flexible tube section 2a is urged to advance in a forward direction as indicated by an arrow in FIG. 8 because of a reduction of resistance against a forward movement. In this manner, the insertion instrument 2 can be advanced smoothly along a path of insertion in an intestinal tract without forcibly pushing the instrument 2. More or less a pushing force can be applied at the time of propelling the rigid tip end section 2c. However, from the standpoint of lessening pains on the part of the patient, it is rather recommendable to slightly pull back the insertion instrument 2 as indicated by an arrow in FIG. 9, thereby straightening the flexible tube section 2a to a certain degree to move the insertion instrument 2 smoothly in the forward direction.

By repeating the above-described manipulation procedure, the endoscopic insertion instrument 2 can be passed securely and smoothly through the large intestine 41, reducing oppressive forces on the intestinal lining wall to a minimum. By adoption of a highly flexible structure for the flexible tube section 2a of the insertion instrument 2, especially at its joint portion with the articular section 2b, the insertion instrument 2 can be passed through the large intestine more smoothly, reducing oppressive forces on the intestinal lining wall to a minimum while maximizing the stretchability potential reserve R. Besides, the insertion instrument can be advanced in such a way as to relieve the intestinal lining wall of a pushing force which is exerted by the instrument 2, and to restore a natural state in transit as the insertion instrument 2 is passed through the intestinal tract, thereby preventing accumulation of pushing forces on the lining wall. Thus, the resistance against passage of the insertion instrument 2 will not increase to a material degree even when the instrument 2 is advanced from the descending colon 44 to the transverse colon 45 and then to the ascending colon 46. Accordingly, the insertion instrument 2 can be passed easily through the acutely bent transitional part from the transverse colon to the ascending colon 46 in advancing the rigid tip end section 2c of the instrument 2 as far as the cecum 47 without applying excessively large oppressive forces on the intestinal lining wall, while lessening the burden on the part of the operator.

Figure 10:
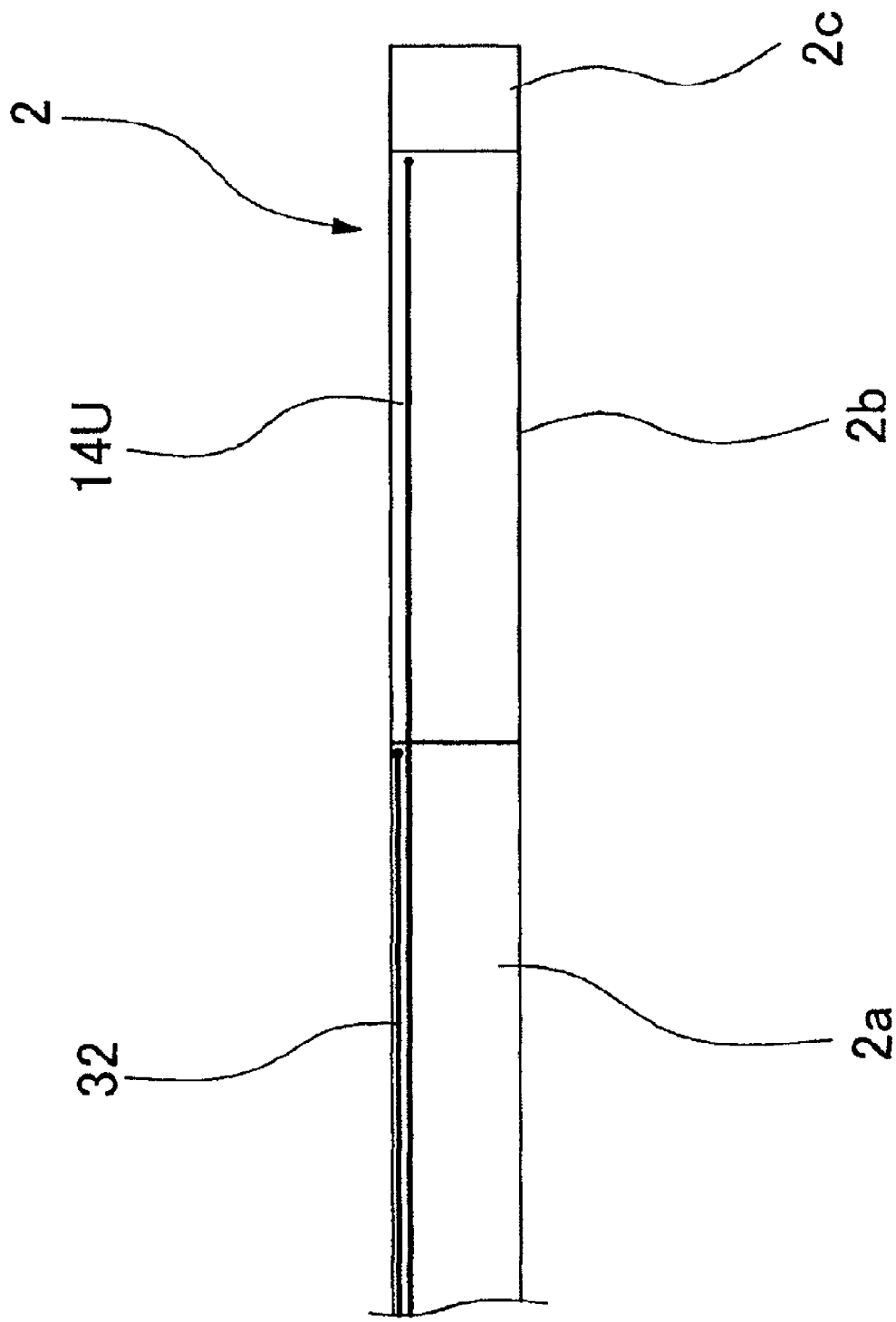
FIG. 10 is a schematic illustration of another specific example of positions for connecting fore distal ends of flexing wire and straightening wire.
Figure 11:
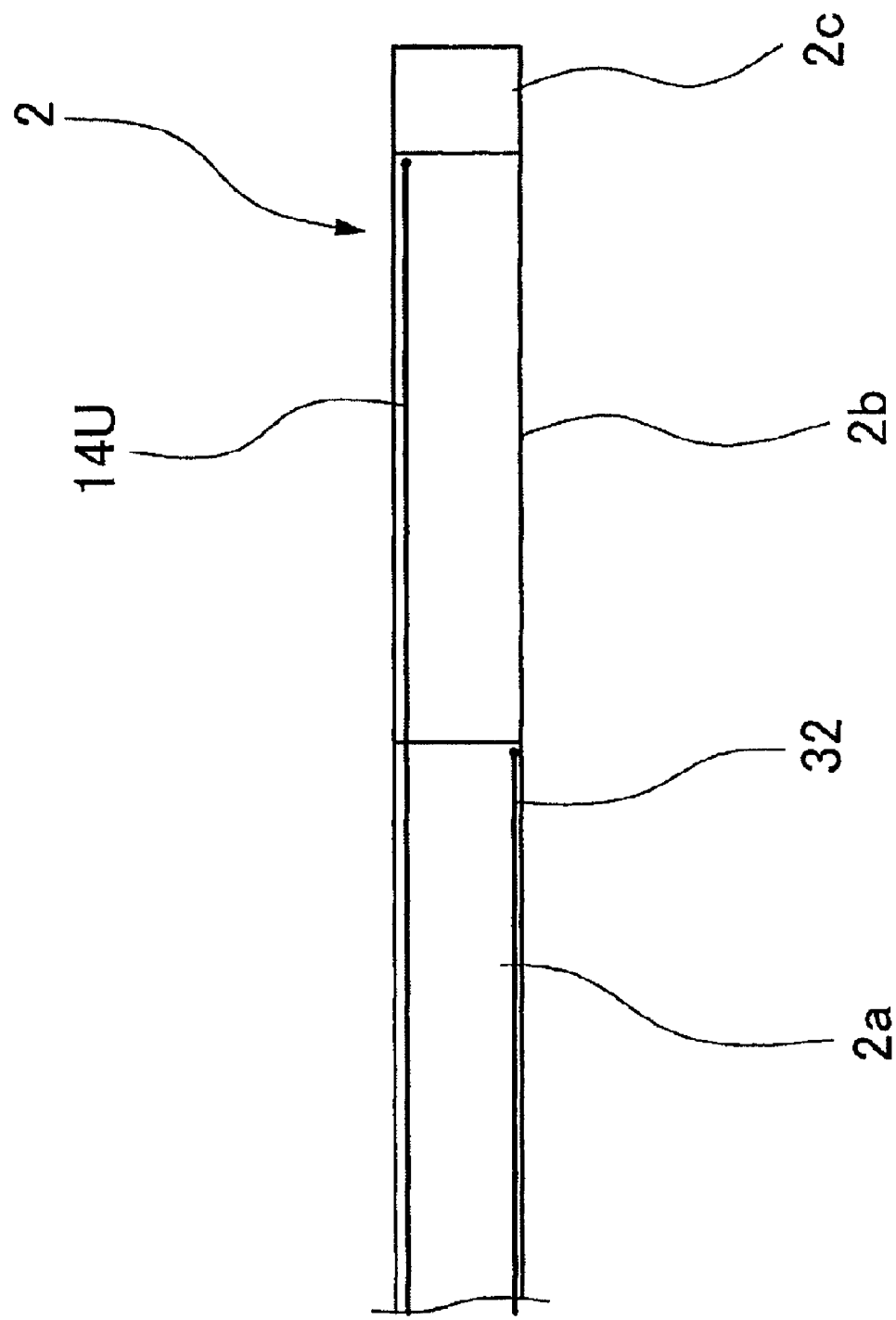
FIG. 11 is a schematic illustration of a third specific example of positions for connecting fore distal ends of flexing wire and straightening wire.
Figure 12:
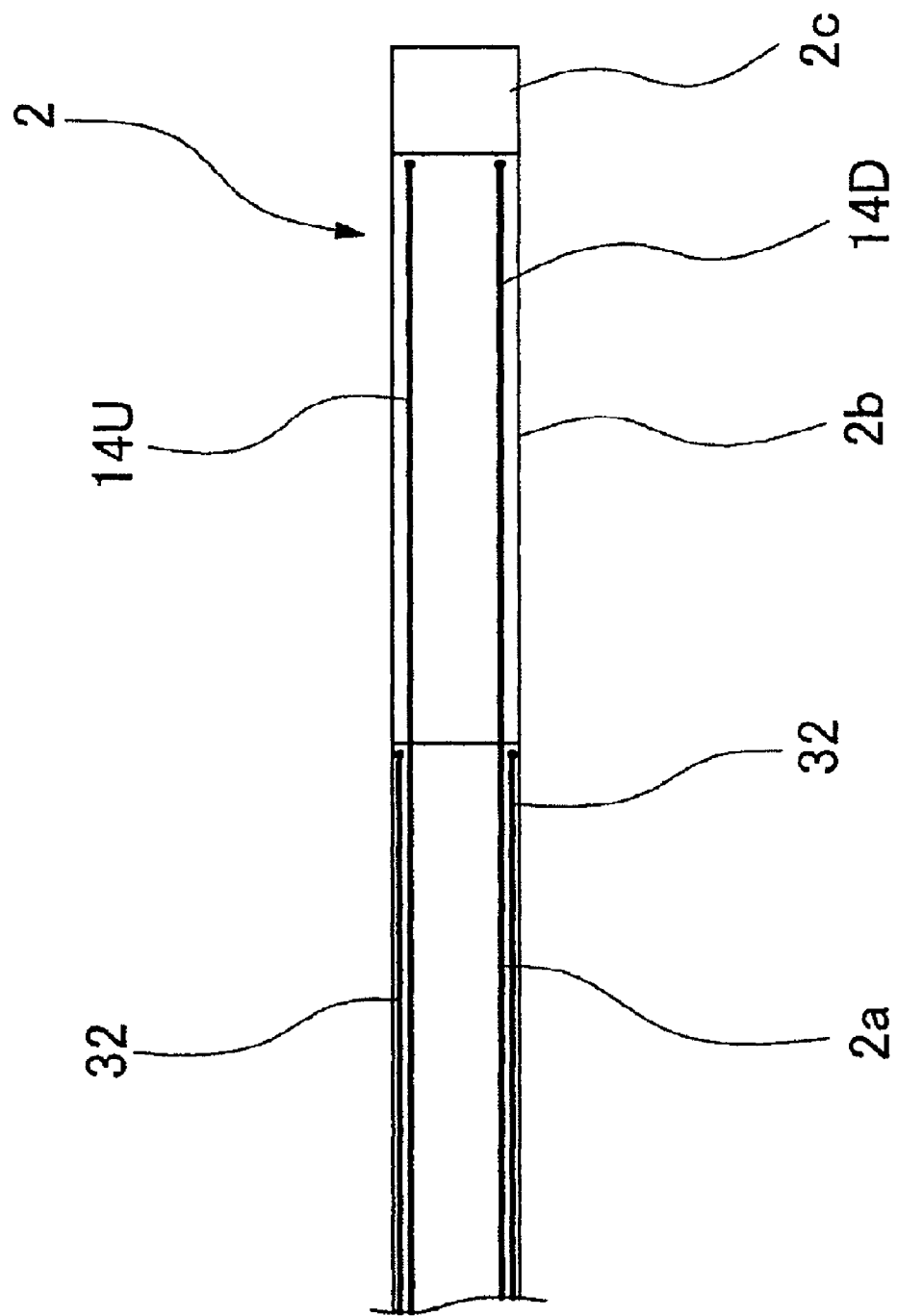
FIG. 12 is a schematic illustration a fourth specific example of positions for connecting fore distal ends of flexing wire and straightening wire.
Figure 13:
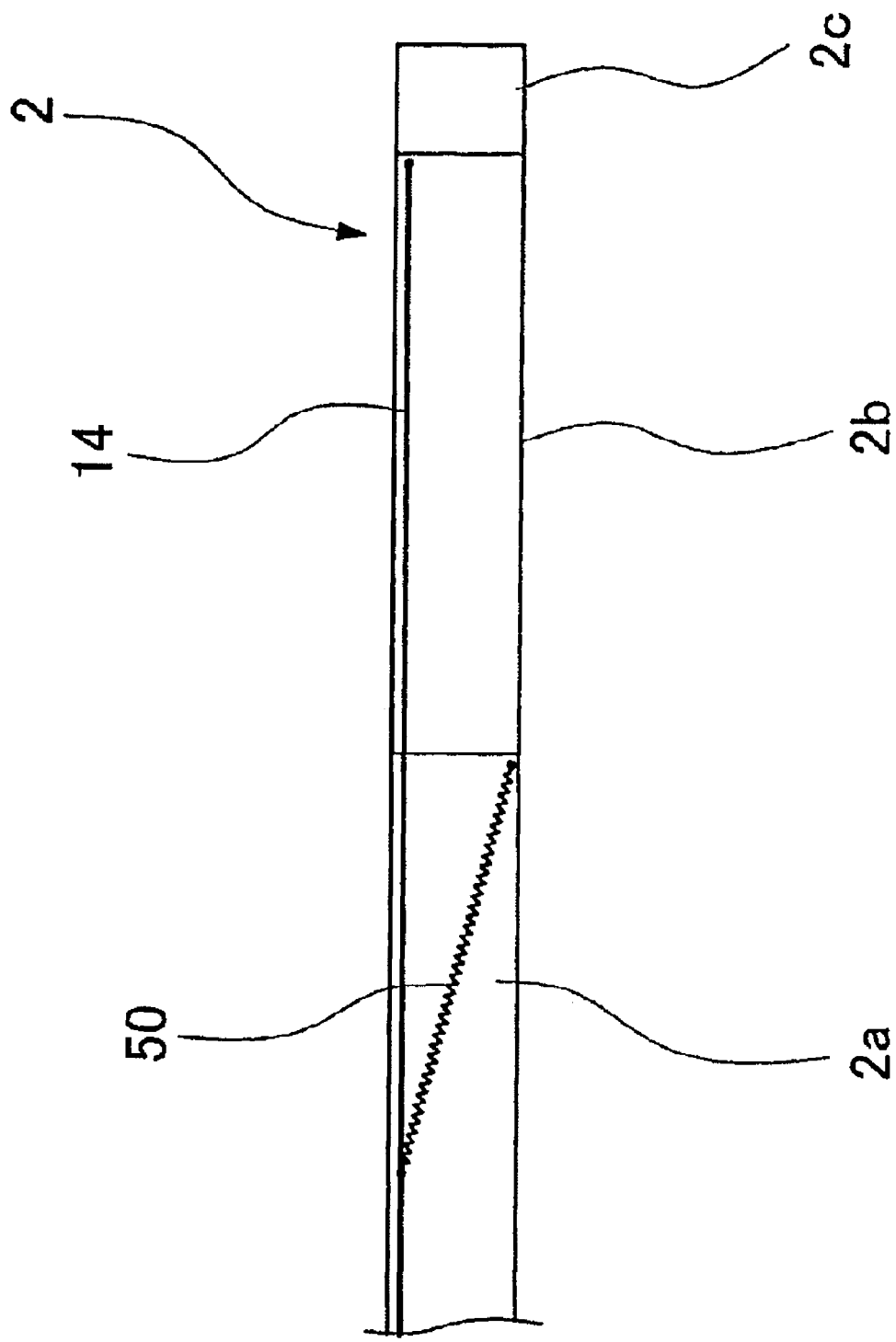
FIG. 13 is a schematic illustration of a fifth specific example of positions for connecting fore distal ends of flexing wire and straightening wire.
Figure 14:
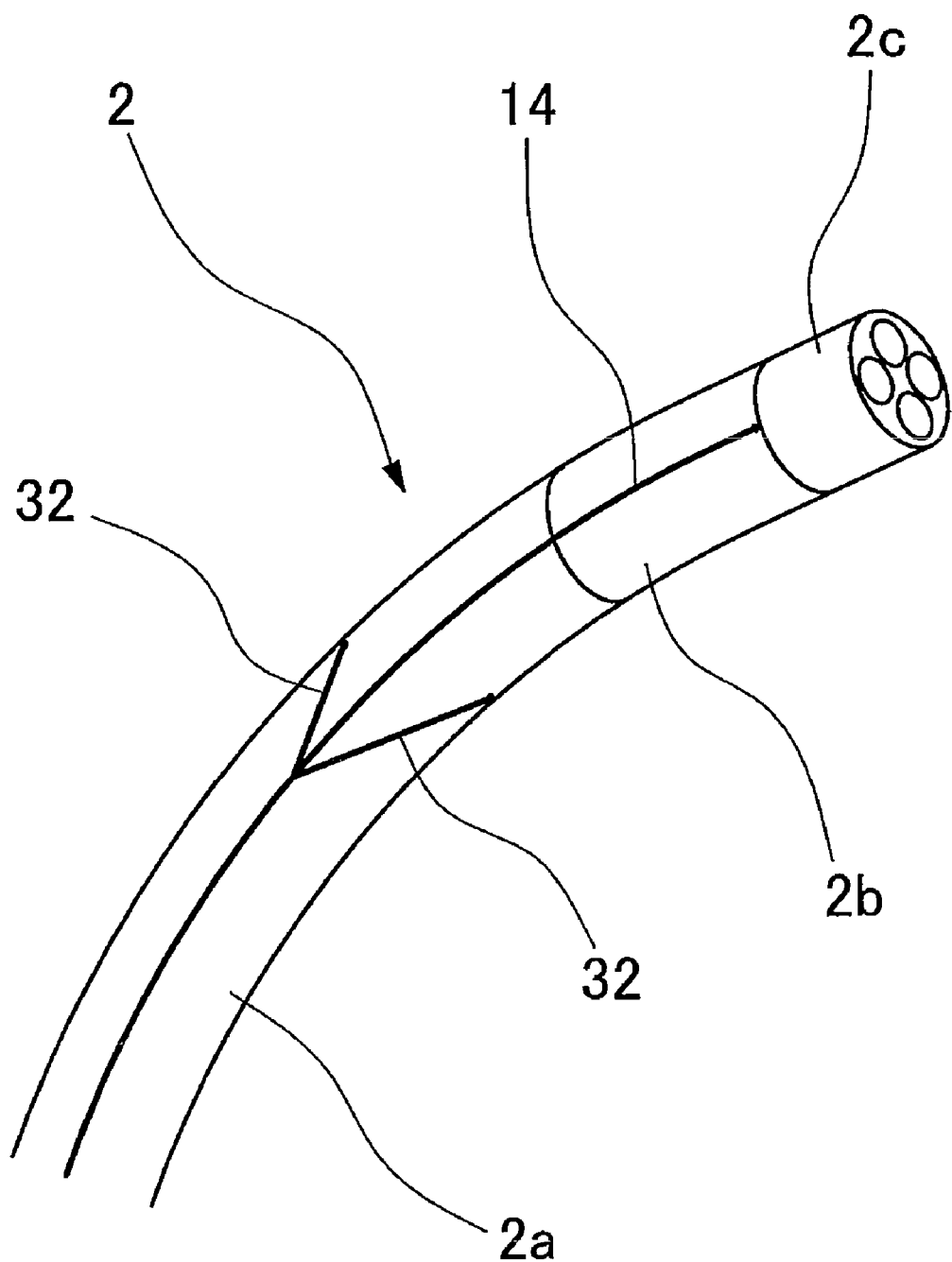
FIG. 14 is a schematic illustration of a sixth specific example of positions for connecting fore distal ends of flexing wire and straightening wire.

In the above-described embodiment, the traction wire 32 for straightening the flexible tube section 2a is located side by side and operationally interlinked with manipulation of the flexing wire 14D which is pulled at the time of flexing the articular section 2b in a downward direction. However, it is possible to adopt a modification having the traction wire for straightening the flexible tube section 2a located side by side and operationally interlinked with manipulation of the upwardly flexing wire 144U as shown in FIG. 10, or alternatively a modification having the traction wire 32 located in a 180 degrees shifted position relative to the upwardly flexing wire 14U as shown in FIG. 11. Further, it is possible to adopt another modification having a couple of traction wires 32 which are respectively arranged to run side by side with upwardly and downwardly flexing wires 14U and 14D as shown in FIG. 12. Alternatively, there may be adopted a modification employing a flexing wire 14 which also functions as a traction wire in cooperation with a tension spring 50 which is connected between a fore end portion of the flexing wire 14 and the connector ring 13 as shown in FIG. 13. Further, there may be adopted a modification linking a couple of traction wires 32 with a flexing wire 14 as shown in FIG. 14.

Figure 15:
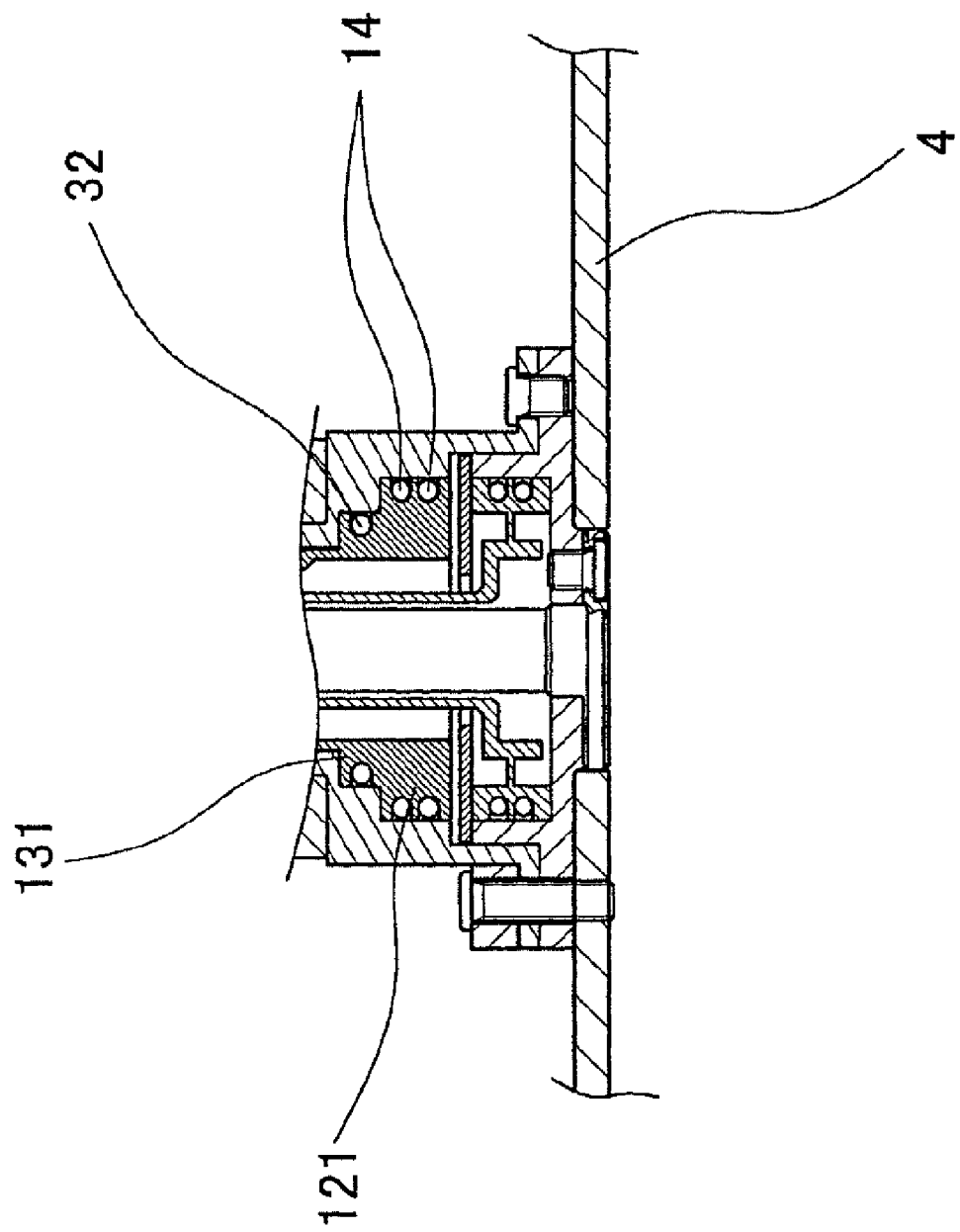
FIG. 15 is a schematic illustration explanatory of a modification of a mechanism interlinking a straightening pulley with a flexing pulley.

Further, in the above embodiment, a straightening pulley is coupled with the outer shaft separately from a flexing pulley in the above-described embodiment. If desired, a flexible tube straightening pulley 131 may be provided on one integral structure along with a first flexing pulley 121 as in a modification shown in FIG. 15.

Figure 16:
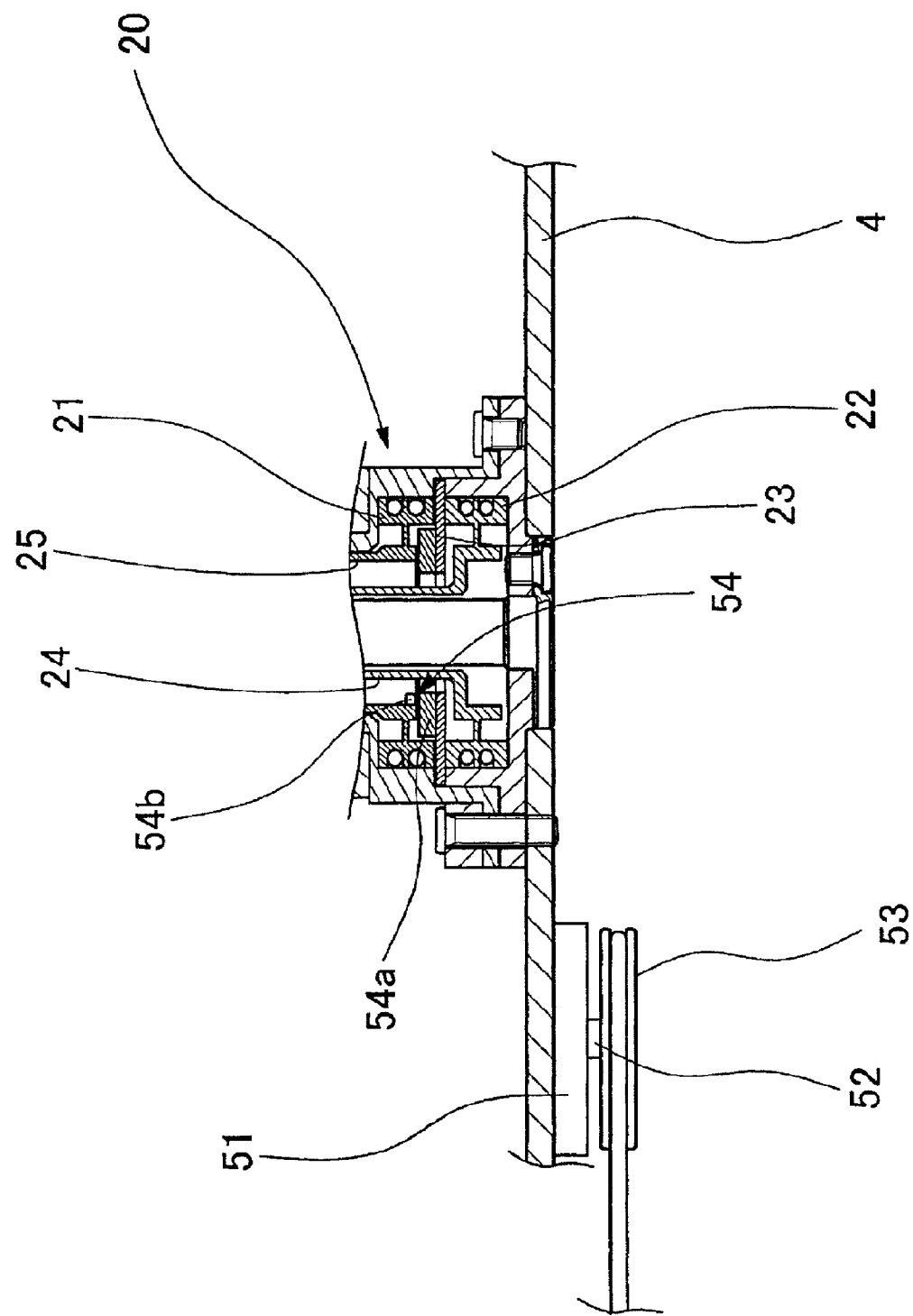
FIG. 16 is a fragmentary sectional view showing particulars in another embodiment of the invention.

Further, as in a modification shown in FIG. 16, it is possible to couple a flexible tube straightening pulley 53 with an ultrasonic motor 51 which is mounted on a support plate 4 within a casing of a manipulating head 1 of an endoscope. In this instance, operation of the ultrasonic motor 52 is interlinked with a rotational movement of a first flexing pulley 21. Namely, in this case, a flexion control means 20 is provided with a rotation detection means 54 between an outer shaft 25 and a spacer plate 23 which is interposed between first and second flexing pulleys 21 and 22. The rotation detection means 54 is constituted by a rotation detector plate 54a which is fixed on the spacer plate 23, and a sensor 54b which is mounted on the outer shaft 25. The sensor 54b is connected with the ultrasound motor 51 via a mode selector switch 51 thereby to switch the operation of the flexion control means 20 to and from an interlinked flexing mode in which a flexing operation is interlinked with activation of the ultrasonic motor 51 and a non-interlinked flexing mode in which a flexing operation is feasible independently of the ultrasonic motor 51.

By adoption of the arrangements just described, the flexion control means 20 of the endoscope becomes operable either in a non-interlinked flexing mode in which the articular section 2b of the endoscopic insertion instrument 2 is flexed in an ordinary operating mode without accompanied by an action of straightening the flexible tube section 2a of the insertion instrument 2 or in an interlinked flexing mode in which straightening of the flexible tube section 2a takes place in interlinked relation with a flexing operation by the flexion control means 20, straightening the flexible tube section 2a in relation with a flexion of the articular section 2b to bring the insertion instrument out of intimate contact with an intestinal lining wall, letting the insertion instrument pass smoothly and securely through a tortuous path of insertion.

The invention claimed is:

1. An endoscope having an elongated insertion instrument for introduction into a body cavity, said insertion instrument being connected at a proximal end to a manipulating head grip and being composed of an elongated flexible tube section, an articular section and a rigid tip end section in series from said proximal end, said articular section being angularly flexed in a desired direction by way of a manual operation of at least one flexing wire around a flexing pulley comprising of manual flexion control means on said manipulating head grip, wherein a flexible tube straightening means is incorporated into said flexible tube section to straighten up a curved bend in said flexible tube section on the proximal side of said articular section;

said straightening means is coupled with said flexion control means via an interlinking mechanism adapted to activate and deactivate said straightening means in interlinked relation with a flexing operation by said flexion control means;

said straightening means comprises a traction wire having one end thereof fixedly connected to a joint portion of said flexible tube with said articular section and having other end wrapped around a straightening pulley; and said flexible tube straightening means is arranged to have a play in length in a span between a fixed fore end and a proximal end portion wrapped around said straightening pulley to delay a straightening action relative to a flexing action by said flexion control means.

2. An endoscope as set forth in claim 1, wherein said traction wire being located in a predetermined radial position within said flexible tube section by a number of positioning members.

3. An endoscope as set forth in claim 2, wherein said traction wire is passed through a number of threading pipes fixedly provided in a predetermined pitch on an inner coil tube serving as a structural member of said flexible tube section.

4. An endoscope as set forth in claim 2, wherein said flexion control means is comprised of said at least one flexing wire having one end thereof fixedly connected to said fore end portion of said articular section and having the other end wrapped around said flexing pulley, a rotational shaft coupled with said flexing pulley, and a control knob for turning said rotational shaft, and said straightening pulley is adapted to be rotationally driven from said rotational shaft, said straightening pulley being equivalent with or smaller than said flexing pulley in diameter.

5. An endoscope as set forth in claim 2, wherein said traction wire is arranged to run internally of said flexible tube section side by side with one of said at least one flexing wire of said flexion control means.

6. An endoscope as set forth in claim 5, wherein said traction wire is connected to an intermediate portion of a flexing wire in such a way as to form a single wire assembly with the latter.

7. An endoscope as set forth in claim 2, wherein said at least one flexing wire includes upwardly and downwardly flexing wires, and a couple of traction wires are arranged to run internally of said flexible tube section, side by side with said upwardly and downwardly flexing wires of said flexion control means, respectively.

8. An endoscope as set forth in claim 2, wherein said straightening pulley is adapted to be driven from an electric motor under control of an interlinking mechanism, which interlinking mechanism being arranged to activate said motor with a predetermined delay from a start of a flexing operation by said flexion control means.

9. An endoscope as set forth in claim 2, wherein said interlinking mechanism is provided with a mode selector switch to switch a mode of operation between an interlinked mode in which an electric motor is turned on and off in interlinked relation with a flexing operation by said flexion control means and a non-interlinked mode in which said electric motor is put at rest irrespective of a flexing operation by said flexion control means.

10. An endoscope as set forth in claim 1, wherein said flexion control means is adapted to flex said articular section in upward, downward, rightward and leftward directions, and said straightening means is adapted to straighten said flexible tube section in interlinked relation with an upward or downward flexing operation of said flexion control means.

11. An endoscope as set forth in claim 1, wherein said play in length of said traction wire is created by the use of a slack-absorbing member having a slack-absorbing spring incorporated into a tubular case.

* * * * *